United States Patent [19]

Bernhardt et al.

[11] 4,335,052
[45] Jun. 15, 1982

[54] METHOD OF PREPARING SUBSTITUTED BENZALDEHYDES

[75] Inventors: Günther Bernhardt, St. Augustin; Egon-Norbert Petersen, Neunkirchen; Gerhard Daum, Cologne, all of Fed. Rep. of Germany

[73] Assignee: Dynamit Nobel Aktiengesellschaft, Troisdorf, Fed. Rep. of Germany

[21] Appl. No.: 210,469

[22] Filed: Nov. 24, 1980

[30] Foreign Application Priority Data

Nov. 29, 1979 [DE] Fed. Rep. of Germany ....... 2948058

[51] Int. Cl.$^3$ ..................... C07C 121/76; C07C 45/28
[52] U.S. Cl. .......................... 260/465 R; 260/465 D; 260/465 F; 260/465 G; 260/465 H; 560/109; 560/130; 568/316; 568/436
[58] Field of Search ..................... 568/436; 260/465 R

[56] References Cited

U.S. PATENT DOCUMENTS 3,157,703  11/1964  Franzen et al. ................. 568/436 X

OTHER PUBLICATIONS

Franzen et al., Ber., vol. 94, pp. 1360-1363 (1961).
Feely et al., J. Org. Chem., vol. 22, p. 1135 (1957).

Primary Examiner—Dolph H. Torrence
Attorney, Agent, or Firm—Sprung, Horn, Kramer & Woods

[57] ABSTRACT

A process for the preparation of Benzaldehydes substituted in the nucleus is disclosed by oxidation of the corresponding benzyl halides. The process is performed in the presence of water using aminoxides of tertiary amines.

13 Claims, No Drawings

METHOD OF PREPARING SUBSTITUTED BENZALDEHYDES

BACKGROUND OF THE INVENTION

1. Field of the Invention

The subject matter of the present invention is a method for the production of benzaldehydes, in which the corresponding benzyl halides are oxidized to the aldehyde.

2. Discussion of Prior Art

It is known to perform the oxidation of benzyl halides to benzaldehydes by means of organic oxidants. The disadvantage of this method lies in the long reaction times and the low yields. Furthermore, the working up of the reaction products often involves great difficulty.

Trimethylamine-N-oxide has already been proposed as an organic oxidant for the transformation of unsubstituted benzyl bromide to benzaldehyde [Ber. 94 (1961), p. 1360]. A disadvantage of this procedure is the use of a great excess of aminoxide, which has to be used in the anhydrous state, inasmuch as it has a tendency toward spontaneous, explosive decomposition. Furthermore, this method also has the disadvantage of the low yield of under 50%.

It is furthermore known to use pyridine-N-oxide as an organic oxidant in the oxidation of benzyl halides to benzaldehydes [J. Org. Chem. 22 (1957), p. 1135]. A disadvantage in this procedure is the fact that the quaternary salt forming as an intermediate from pyridine oxide and the benzyl halide is stable and it can be cleaved to benzaldehyde and pyridine only by an additional treatment with dilute caustic soda solution. In this procedure, which also has to be performed with anhydrous pyridine oxide, the yields are only around 40%.

The problem, therefore, existed of performing the oxidation of benzyl halides to benzaldehydes technically such that high yields of pure product are obtained, the reaction being performed in a single step, if possible, and with easily available compounds. Furthermore, the desired process should be applicable especially to the production of benzaldehydes substituted in the nucleus, whose preparation is made more difficult in the case of an ortho substitution of electron-attracting substituents.

SUMMARY OF THE INVENTION

As a solution of this problem, a method has been found for the preparation of benzaldehydes substituted in the nucleus by oxidation of the corresponding benzyl halides, this method being characterized by performing the oxidation in the presence of an amine oxide of a tertiary amine at a temperature between 40° and 140° C. in the presence of water.

In this procedure, the disadvantage of the known methods are non-existent or they exist to only a very slight degree. The yields of aldehydes are considerably higher than in the known methods, and they are furthermore obtained in a substantially shorter reaction time. These high yields are independent of the nature of the substituents of the benzyl halide and of the purity of this substance. Accordingly, a benzyl halide can also be used which contains the corresponding benzal halide and/or the corresponding methylbenzene.

The method of the invention furthermore has the advantage that easily preparable compounds can be used as starting products. This applies not only to the benzyl halides but also to the aminoxides. When the latter are produced they are in the form either of aqueous solutions or of hydrates. The solutions can be used directly without special purification.

The water that is present in the reaction is best added to the reaction mixture together with the aminoxide, which is used either in the form of its hydrate or in the form of an aqueous solution. The amount of water thus put into the reaction mixture can be between 0.1 to 50% water with respect to the total volume of the reaction mixture. Preferably, however, the amount of water to be added is selected such that the water content in the reaction mixture is between 0.5 and 25% by volume.

The reaction of the benzyl halide with the aminoxide takes place with stoichiometric amounts. It is sufficient, therefore, to use the reactants in the equivalent ratio, 1:1. It is recommendable, however, to apply the aminoxide in a slight excess, so that 1 to 1.5 equivalents, for example, of aminoxide can be used per equivalent of benzyl halide. The excess of the aminoxide, however, can also be greater, although preferable it should not exceed two equivalents per equivalent of benzyl halide.

The reaction temperature is generally between 20° and 140° C. It is preferred, however, to operate in the range between 40° and 100° C. At the same time it is recommendable to perform the reaction at the boiling temperature of the solvent used, although another, higher-boiling solvent can also be used, provided the stated temperature limits are maintained during the reaction.

Suitable solvents and reaction media include virtually all liquid compounds in which the benzyl halides are soluble. Preferably the solvents and reaction media are inert to the components of the reaction mixture under the prevailing reaction conditions. These include aliphatic, cycloaliphatic and aromatic hydrocarbons, chlorinated hydrocarbons, alkyl cyanides, carboxylic acid esters, aliphatic alcohols, nitrated hydrocarbons, preferably nitroaromatics and mixtures of these compounds. It is not necessary that the organic solvent be miscible with water. Even when aminoxide and benzyl halide are dissolved in two different phases, the reaction takes place in the desired direction. Needless to say, provision must be made in that case for a long, intimate contact between the two phases, e.g., by stirring.

The following are mentioned as examples of solvents which can be used: carbon tetrachloride, 1,2-dichloroethane, chloroform, hexane, cyclohexane, toluene, acetonitrile, acetic acid methyl ester, acetic acid butyl ester, acetic acid amyl ester, propionic acid ethyl ester, methanol, ethanol, the butanols, the chlorobenzenes and nitrotoluenes. The solvents are to have, if possible, a boiling point below 150° C.

The performance of the process of the invention is conducted in a manner known in itself. Either one of the two reaction components is placed together with the reaction medium in a suitable reaction vessel and the second component is fed to it during the course of the reaction, or both components can be placed simultaneously in the reaction medium. It is desirable to feed in the aminoxide in the form of an aqueous solution. It is recommendable, before feeding in either or both of the reaction components, to bring the contents of the reaction vessel to the reaction temperature that is to prevail. Then the reaction mixture is kept in good movement, for example by stirring. Depending on the concentration of the reactants, the reaction is completed in half an hour to three hours. The end of the reaction can be determined by gas chromatography or gravimetry (reaction of the unreacted benzyl halide with pyridine).

If the reaction medium is greatly diluted by water, it is recommendable to remove excess water from the reaction chamber, i.e., the water not needed for the reaction. It is preferable to do this whenever the proportion of the water amounts to more than 25% of the total volume.

The removal of the water can be accomplished, for example, by using as the reaction medium a solvent which forms an azeotrope with water, such as toluene, for example, or carbon tetrachloride, chloroform or 1,2-dichloroethane. The reaction is then performed at the boiling point of this azeotrope. The azeotrope is then distilled out and the separated solvent can then be recycled to the reaction mixture if desired.

It is also possible, however, to concentrate excessively diluted aqueous aminoxide solutions prior to their use in the process of the invention, by means of suitable drying agents or by removing the water at reduced pressure or by azeotropic distillation with a suitable solvent to the concentration desired for the reaction.

The reaction mixture is worked up in a manner known in itself. At the end of the reaction, such an amount of water is added to the reaction mixture that any precipitated ammonium salts are dissolved and the aqueous phase can be separated from the organic phase. The organic phase thus obtained is treated with dilute mineral acid, then neutralized with dilute bases, and then washed with water. The isolation of the aldehyde is performed by distillation of the solvent. For the purification of the aldehyde, a distillation or recrystallization can be performed. If desired, an intermediate isolation and purification of the aldehyde can be accomplished through the bisulfite compound.

It is furthermore possible to recover the amine in a known manner from the aqueous ammonium halide solution obtained, during the above mentioned working-up of the reaction mixture by adding bases to this solution. Preferred suitable bases are the corresponding alkali and alkaline earth compounds. The amine set free in this manner can then, after its isolation, be recycled to the production of the aminoxide.

The aminoxides of tertiary amines which can be used in accordance with the invention are the aminoxides of aliphatic, cycloaliphatic, aromatic or heterocyclic tertiary amines. Also the aminoxides of bivalent tertiary amines can be used. The total number of the carbon atoms of the aminoxides, however, is to be preferably greater than three, since otherwise the yields are too low unless additional measures are taken. Generally the number of carbon atoms in each organo group bound to the nitrogen atom of the amine is 1 to 18, with the proviso that at least one of the organo groups has at least two carbon atoms. Preferred organo groups are alkyl, aralkyl, cycloalkyl, aryl in addition to moieties making up a heterocyclic structure. These organo groups can be substituted one or more times by any of the following groups: cyano, nitro, halogen, (only in aromatic nuclei), $C_{1-8}$ alkoxy.

Suitable aminoxides with aliphatic moieties, which can be substituted if desired, are, for example, triethylamine-N-oxide, tripropylamine-N-oxide, tributylamine-N-oxide, isopropyldiethylamine-N-oxide, tri-($\beta$-ethoxyethyl)-amine-N-oxide and $\beta$-diethylaminopropionitrile-N-oxide. An aminoxide with a cycloaliphatic moiety is, for example, dimethylcyclohexylamine-N-oxide. The preferred aminoxide is triethylamine-N-oxide.

Suitable aminoxides with aromatic moieties are, for example, dimethylaniline-N-oxide, benzylmethylaniline-N-oxide, p-nitrophenyldiethylamine-N-oxide and p-N,N-diethylaminobenzonitrile-N-oxide.

Suitable heterocyclic aminoxides are, for example, N-alkyl- or N-aryl-morpholine-N-oxides, such as N-butylmorpholine-N-oxide, N-phenylmorpholine-N-oxide, N-aryl- or N-alkyl-tetrahydroquinoline-N-oxide, N-aryl- or N-alkyl-pyrrolidine-N-oxides and their derivatives, e.g., N-methylpyrrolidine-N-oxide and N-phenylpyrrolidine-N-oxide.

Suitable bivalent tertiary aminoxides are: N,N,N',N'-tetraethylethylenediamine-N,N'-dioxide, N,N'-dimethyl-N,N'-dibenzylhexamethylenediamine-N,N'-dioxide and triethylenediamine-N,N'-dioxide.

The benzyl halides mono- or polysubstituted in the benzene ring, which can be used as starting compounds, can be characterized by the following general formula:

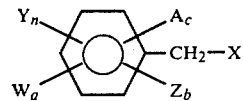

In this formula,
A = nitro groups and/or nitrile groups and/or acyloxy and/or acyl groups (c = 0 to 2)
Y = halogen, especially chlorine and/or bromine, and/or alkyl groups (n = 0 to 5)
W = —CH$_2$—X (a = 0 to 5, preferably 0 to 3)
Z = —OH and/or alkoxy and/or phenoxy groups (b = 0 to 3), the sum of a + b + n + c being equal to 1 to 5, preferably 1 to 3, and
X = chlorine, bromine or iodine.

The moiety A is preferably a nitro group in the ortho position.

In detail, the following are mentioned as benzyl halides substituted in the nucleus:
o-, m- or p-nitrobenzyl bromide,
2,4-dinitrobenzyl bromide,
o-, m- or p-cyanobenzyl bromide
o-, m- or p-chloro- or bromobenzyl bromide,
trichloro- or tribromobenzyl bromide,
tetrachloro- or tetrabromobenzyl bromide,
pentabromo- or pentachlorobenzyl bromide,
o-, m- or p-phenoxybenzyl bromide,
o-, m- or p-methylbenzyl bromide,
2,4-dimethylbenzyl bromide,
2,4,6-trimethylbenzyl bromide,
o- or m- or p-hydroxybenzyl bromide,
o- or m- or p-methoxybenzyl bromide,
3,4,5-trimethoxybenzyl bromide,
as well as the corresponding chlorides of the named compounds.

Additional substituted bromides, chlorides and iodides which can be reacted by the method of the invention are those which have an additional —CH$_2$X— substituent in the ortho, meta or para position, such as for example o-, m- or p-xylylene dibromide or dichloride, and furthermore those compounds which have, in addition to the —CH$_2$—X— substituent, one or more substituents in the benzene nucleus, such as bromine or chlorine substituents, such as, for example, tetrachloroxylylene dibromide or dichloride, tetrabromoxylylene dibromide or dichloride, the corresponding monochloro, dichloro and trichloroxylylene dibromides, and the corresponding dichlorides.

Also, alkyl-substituted xylylene dihalides, such as for example $C_1$ to $C_2$-dialkyl-substituted xylylene dihalides, such as dimethyl- or diethylxylylene dihalides, dialkoxysubstituted xylylene dihalides, such as dimethoxyxylylene dihalides, and the corresponding hydroxy-substituted xylylene dihalides such as mono- and dihydroxyxylylene dihalides, can be reacted.

An especially advantageous and simple embodiment of the method of the invention consists in reacting the crude halogenation mixtures of substituted toluenes, containing, if desired, unmodified starting material or benzal halide in addition to the corresponding benzyl halide, with aminoxides, and, after separating the aldehyde, returning the unmodified, substituted toluene to the halogenation process. Thus, for example, the halogenation of the toluene and the subsequent reaction with the aminoxide can be performed in the same solvent and reaction vessel in a one-pot process.

In the preparation of air-sensitive aldehydes, it is advantageous to add known antioxidants to the reaction mixture toward the end of the reaction. Air-sensitive aldehydes are, for example, those which contain positivizing groups, such as, for example, one or more methyl groups. Amounts between 0.01 and 3.0% of the weight of the reaction mixture suffice to prevent the self-oxidation of the aldehyde. Suitable antioxidants are basically the known antioxidants such as sterically hindered phenols, for example, 2,6-di-tert-butylphenol being named as an example.

The compounds which can be produced in accordance with the present invention are valuable intermediates for the manufacture of pharmaceuticals, herbicides, flame-proofing agents, dyes and optical brighteners. Especially o-nitrobenzaldehyde, which is obtainable by the method of the invention, has for years been an important intermediate whose technical manufacture has thus far been unsatisfactory on account of the low yields achieved in the processes known previously.

EXAMPLE 1

In a three necked flask equipped with reflux condenser, thermometer and stirrer, 180 g of aqueous triethylamine-N-oxide (75%, equal to approximately 1.15 mol) and 1000 ml of carbon tetrachloride were placed, and over a period of 5 minutes 216 g of o-nitrobenzyl bromide (1.0 mol) was added with thorough stirring.

The mixture was refluxed for $2\frac{1}{4}$ hours, and after cooling, 100 ml of water was added. After separation of the aqueous phase, the carbon tetrachloride solution was treated with 100 ml of 2 N HCl, then washed thrice with 100 ml of water, the carbon tetrachloride was distilled out, and the residue, consisting already of 97% of the desired product according to gas chromatography, was subjected to a vacuum distillation.

At 0.4 mm and 84° to 86°, 128.2 g of o-nitrobenzaldehyde passed over, equal to approximately 85% of the theory, and its melting point was 40°–41° C.).

EXAMPLES 2a TO 2d

The same procedure was followed as in Example 1, except that the solvents listed in Table 1 were used instead of carbon tetrachloride:

TABLE 1

| | | o-nitrobenzaldehyde | |
|---|---|---|---|
| Example | Solvent | Yield [% of the theory] | M.P. [°C.] |
| 2 a | methanol | 73.7 | 40–41 |
| 2 b | methylene chloride | 80.5 | 41–42 |
| 2 c | ethylene dichloride | 81.3 | 40–41 |
| 2 d | acetonitrile | 75.0 | 39–40.5 |

EXAMPLE 3

2639 g of a bromination mixture consisting of 311 g of o-nitrobenzyl bromide (1.44 mol), 21 g of o-nitrobenzal bromide (0.007 mol), 332 g of o-nitrotoluene (2.42 mol) and 1975 g of carbon tetrachloride was refluxed in a four-necked flask provided with stirrer, thermometer, dropping funnel, reflux condenser and water separator. Over a period of one hour, 359.7 g of a 54% aqueous solution of triethylamine-N-oxide was added drop by drop, 150 ml of water being removed by azeotropic distillation. Then refluxing was continued for another hour and a half.

The precipitated triethylamine hydrobromide was redissolved with the barely necessary amount of water and, after cooling, the aqueous phase was separated. After the organic phase had been washed with dilute hydrochloric acid and water, carbon tetrachloride was distilled off and the residue was fractionally distilled in vacuo. At $B.P._{0.4}$: 84°–85° C., 174.4 g of o-nitrobenzaldehyde passed over, which is approximately 80.2% of the theory with respect to the o-nitrobenzyl bromide put in.

The o-nitrotoluene that passed over in the first runnings weighed 315 g and corresponds to 95% of the amount contained in the bromination mixture.

The separated aqueous phase was dripped into excess dilute soda lye and the triethylamine that was released was distilled out. After drying and purifying by distillation, 117.3 g of the product was obtained, equal to approximately 80% of the theory.

The o-nitrotoluene and triethylamine can be used for the bromination and for the preparation of the aminoxide, respectively.

EXAMPLE 4

In a four-necked flask equipped with reflux condenser, thermometer, dropping funnel and stirrer, 108 g of p-nitrobenzyl bromide (0.5 mol) and 500 ml of carbon tetrachloride were heated at ebullition, with stirring, and, over a period of 30 minutes, 90.3 g of 75% aqueous triethylamine-N-oxide (approx. 0.58 mol) was added drop by drop. After the addition was completed, the refluxing was continued for two more hours.

After the addition of 100 ml of water, the precipitate was removed by suction filter and two washings were performed with 50 ml of water. From the filtrate consisting of two phases, the organic phase was separated and was then washed with 50 ml of 2 N HCl and then thrice with 50 ml of water. After drying over sodium sulfate, the carbon tetrachloride was removed by evaporation and the residue from the evaporation was combined with the filter cake.

The total yield of p-nitrobenzaldehyde amounted to 60.6 g, corresponding to a yield of 80.2% of the theory (M.P. 103°–104° C.).

EXAMPLE 5

The procedure of Example 4 was performed, except that 400 ml of acetic acid ethyl ester was used as the solvent instead of carbon tetrachloride.

The yield of p-nitrobenzaldehyde amounted to 71.0% of the theory (M.P. 102°–104° C.).

EXAMPLE 6

In a three-necked flask provided with stirrer, reflux condenser and thermometer, 20.4 g of 2,4,6-tribromobenzyl bromide (approx. 0.05 mol), 50 ml of 1,2-dichloroethane and 9.4 g of aqueous triethylamine-N-oxide (75% solution equal to about 0.06 mol) were heated for three hours at ebullition.

After the addition of 30 ml of water, the organic phase was separated and washed with 30 ml of water. After removal of the 1,2-dichloroethane by evaporation and recrystallization of the residue from 55 ml of isopropanol, 14.1 g (82.0% of the theory) of 2,4,6-tribromobenzaldehyde was obtained, having a melting point of 97°–98° C.

| Elemental analysis: | C | H | Br |
| --- | --- | --- | --- |
| Calculated | 24.89 | 0.87 | 69.95 |
| Found | 25.01 | 0.78 | 69.70 |

EXAMPLE 7

In a four-necked flask equipped with stirrer, dropping funnel, thermometer and reflux condenser, 58.0 g of tetrabromoxylylene dibromide (0.1 mol) was dissolved in 500 ml of toluene; 38.2 g of aqueous triethylamine-N-oxide (76.7% solution, equal to approximately 0.25 mol) was added drop by drop over a period of 20 minutes at 80° to 100° C., and the reaction mixture was held at the above-stated temperature for three more hours.

After the addition of 100 ml of water, the mixture was cooled and the precipitated product was suction filtered. The organic phase was separated from the filtrate consisting of two phases, and concentrated to 100 ml. The product that precipitated upon cooling was removed by suction filtration. The combined and dried filter residues yielded 71.0% of the theory of tetrabromoterephthalic dialdehyde, M.P. 226°–232° C. (from acetone).

| Elemental Analysis | C | H | Br |
| --- | --- | --- | --- |
| Calculated | 21.33 | 0.44 | 71.11 |
| Found | 21.65 | 0.47 | 70.90 |

EXAMPLES 8a–8n

As in Example 1, 1.0 mol of each of the benzyl halides substituted in the benzene ring and listed in Table 2 was reacted in one liter of carbon tetrachloride with 180 g of an aqueous 75% triethylamine-N-oxide solution (1.15 mol) to form the corresponding substituted benzaldehydes.

TABLE 2

| | Substituted benzyl halide | | Aldehyde | | | |
| --- | --- | --- | --- | --- | --- | --- |
| Example | Chemical name | [g] | Yield [g] | [% of theory] | M.P. [°C.] | B.P. [mm/°C.] |
| 8a | p-bromobenzyl bromide | 250.0 | 140.1 | 75.7 | 56–57 | — |
| 8b | o-bromobenzyl bromide | 250.0 | 145.1 | 78.4 | 21.22 | 230 |
| 8c | *pentabromobenzyl bromide | 565.5 | 396.5 | 79.2 | 264–265 | — |
| 8d | o-chlorobenzyl chloride | 161.0 | 91.4 | 65.0 | — | 12/87–88 |
| 8e | 2,4-dichlorobenzyl bromide | 239.9 | 141.8 | 81.0 | 70–71 | — |
| 8f | 2.6-dichlorobenzyl bromide | 239.9 | 148.8 | 85.0 | 70–71 | — |
| 8g | p-cyanobenzyl bromide | 196.1 | 106.6 | 81.3 | 100 | — |
| 8h | m-phenoxybenzyl bromide | 263.1 | 155.0 | 78.2 | — | 12/174–176 |
| 8i | p-benzoyloxybenzyl bromide | 291.2 | 181.2 | 80.1 | 72 | — |
| 8j | p-hydroxybenzyl chloride | 142.6 | 93.9 | 76.9 | 116 | — |
| 8k | 2,4-dimethylbenzyl bromide | 199.1 | 110.7 | 82.5 | — | 12/101–102 |
| 8l | 2,4-dinitrobenzyl bromide | 261.0 | 158.9 | 81.0 | 72 | — |
| 8m | 3,4,5-trimethoxybenzyl chloride | 216.7 | 163.0 | 83.1 | 76–77 | — |
| 8n | 2,4,6-trimethylbenzyl chloride | 168.7 | 125.4 | 84.6 | — | 6/96–98 |

*Solvent toluene

EXAMPLE 9

In the manner described in Example 1, 0.2 mol of o-nitrobenzyl bromide is reacted with the aminoxides listed in Table 3.

TABLE 3

| | | | | o-nitrobenzaldehyde | |
| --- | --- | --- | --- | --- | --- |
| Example | Aminoxide Chemical name | [mol] | Solvent | yield [% of the | [M.P. °C.] |
| a | N,N,N',N'-tetraethylenediamine-N,N'-dioxide 4H$_2$O . | 0.12 | CCl$_4$ | 78.5 | 39.5–41.0 |
| b | N-benzylpiperidine-N-oxide (80% aqueous solution) | 0.23 | CHCl$_3$ (250 ml) | 80.2 | 41–42 |
| c | Dimethylaniline-N-oxide (72% aqueous solution) | 0.22 | CH$_2$Cl$_2$ (200 ml) | 80.5 | 41–42 |
| d | Tripropylamine-N-oxide | 0.25 | CCl$_4$ (300 ml) | 84.8 | 41.5–42 |
| e | N-ethylmorpholine N-oxide | 0.24 | CCl$_4$ (200 ml) | 81.3 | 40–42 |

Example for Comparison 40 g of trimethylamine-N-oxide dihydrate was dissolved in a distillation apparatus in 250 ml of dimethylformamide and heated until the distillate had reached a boiling temperature of 130° C.

The rest of the solvent was distilled off with a waterjet vacuum pump, the heating bath being brought to 125° C.

The yield of trimethylamine-N-oxide amounted to 24.5 grams or approximately 90.7% of the theory.

15 g of the anhydrous trimethylamine oxide thus obtained (0.2 mol) was dissolved in 55 ml of chloroform, and 21.6 g of o-nitrobenzyl bromide (0.1 mol) was added over a period of 10 minutes with ice cooling. Then the mixture was refluxed for another 30 minutes. The cooled reaction solution was treated with 55 ml of 2 N HCl, and then shaken with dilute sodium hydrogen carbonate solution. After drying over sodium sulfate, the chloroform was removed by evaporation at reduced pressure and the residue remaining was vacuum distilled.

At $B.P._{0.4}$ 84°–86°, 6.5 g of o-nitrobenzaldehyde passed over, equal to about 43% of the theory.

What is claimed is:

1. In a process for the preparation of a benzaldehyde substituted in the nucleus by oxidation of the corresponding benzyl halides, the improvement which comprises performing the oxidation in the presence of water with an aminoxide of a tertiary amine at a temperature between 20° and 140° C.

2. A process according to claim 1, wherein the oxidation is performed employing an aqueous aminoxide solution.

3. A process according to claim 1, wherein the oxidation is performed in the presence of 0.1 to 50 vol.-% of water, based upon the total volume of the reaction mixture.

4. A process according to claim 1, wherein there are 1 to 1.5 equivalents of aminoxide per equivalent of benzyl halide.

5. A process according to claim 1, wherein said aminoxide of the tertiary amine is one whose total carbon number is greater than three.

6. A process according to claim 1, wherein the reaction is performed in the presence of an organic solvent.

7. A process according to claim 6, wherein said organic solvent is halogenated aromatic or halogenated aliphatic hydrocarbon.

8. A process according to claim 6, wherein said organic solvent is a nitrated aromatic or aliphatic hydrocarbon.

9. A process according to claim 1, wherein the aldehyde to be prepared is one which is air-sensitive and the reaction mixture contains an anti-oxidant which is added toward the end of the reaction.

10. A process according to claim 1, wherein the benzyl halide is one which is ortho-substituted with an electron attracting substitutent.

11. A process according to claim 1, wherein the benzyl halide is one of the formula

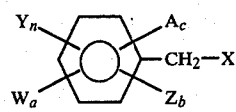

wherein
A denotes nitro groups and/or nitrile groups and/or acyloxy and/or acyl groups (c=0 to 2)
Y denotes halogen, especially chlorine and/or bromine, and/or alkyl groups (n=0 to 5)
W denotes —$CH_2$-X (a=0 to 5, preferably 0 to 3)
Z denotes —OH and/or alkoxy and/or phenoxy groups (b=0 to 3), the sum of a+b+n+c being equal to 1 to 5, preferably 1 to 3, and
X denotes chlorine, bromine or iodine.

12. A process according to claim 1, wherein the aminoxide is triethylamine-N-oxide.

13. A process according to claim 1, wherein the aminoxide is selected from the group consisting of triethylamine-N-oxide, tripropylamine-N-oxide, tributylamine-N-oxide, isopropyldiethylamine-N-oxide, tri-(β-ethoxyethyl)-amine-N-oxide, β-diethylaminopropionitrile-N-oxide, dimethylcyclohexylamine-N-oxide, dimethylaniline-N-oxide, benzyl methylaniline-N-oxide, p-nitrophenyldiethylamine-N-oxide, p-N,N-diethylaminobenzonitrile-N-oxide, N-alkyl-morpholine-N-oxide, N-aryl-morpholine-N-oxide, N-alkyl-tetrahydroquinoline-N-oxide, N-aryl-tetrahydroquinoline-N-oxide, N-alkyl-pyrolidine-N-oxide, N-aryl-pyrolidine-N-oxide, N,N,N',N'-tetraethylethyldiamine-N-N'-dioxide, N,N'-dimethyl-N,N'-dibenzylhexamethylenediamine-N,N'-dioxide and triethylenediamine-N,N'-dioxide.

* * * * *